United States Patent
Wu et al.

(10) Patent No.: US 8,951,304 B2
(45) Date of Patent: Feb. 10, 2015

(54) VACUUM SUCTION STRUCTURE OF ANKLE JOINT AND SUPPORT BARREL OF ARTIFICIAL LIMB

(71) Applicant: Ken Dall Enterprise Co., Ltd., New Taipei (TW)

(72) Inventors: Fu-Kuo Wu, New Taipei (TW); Hsiang-Ming Wu, New Taipei (TW)

(73) Assignee: Ken Dall Enterprises Co., Ltd., New Taipei (TW)

( * ) Notice: Subject to any disclaimer, the term of this patent is extended or adjusted under 35 U.S.C. 154(b) by 9 days.

(21) Appl. No.: 13/920,027

(22) Filed: Jun. 17, 2013

(65) Prior Publication Data
US 2014/0371874 A1    Dec. 18, 2014

(51) Int. Cl.
*A61F 2/80*    (2006.01)
*A61F 2/50*    (2006.01)
*A61F 2/74*    (2006.01)

(52) U.S. Cl.
CPC ........... *A61F 2/80* (2013.01); *A61F 2002/5072* (2013.01); *A61F 2002/742* (2013.01); *A61F 2002/745* (2013.01); *A61F 2002/748* (2013.01); *A61F 2002/802* (2013.01); *A61F 2002/805* (2013.01); *A61F 2002/807* (2013.01)
USPC ........................................................... 623/34

(58) Field of Classification Search
CPC ................... A61F 2002/802; A61F 2002/805; A61F 2002/807
USPC ................. 623/27, 32, 33, 34, 35, 36, 37, 38
See application file for complete search history.

(56) References Cited

U.S. PATENT DOCUMENTS

| | | | | |
|---|---|---|---|---|
| 6,645,253 | B2 * | 11/2003 | Caspers | 623/26 |
| 7,025,792 | B2 * | 4/2006 | Collier | 623/33 |
| 8,007,543 | B2 * | 8/2011 | Martin | 623/34 |
| 2010/0312360 | A1 * | 12/2010 | Caspers | 623/34 |

* cited by examiner

*Primary Examiner* — Marcia Watkins
(74) *Attorney, Agent, or Firm* — Leong C. Lei (57) ABSTRACT

A vacuum suction structure of ankle joint and support barrel of artificial limb is connected, to the top thereof, with an artificial limb and the support barrel and is connected, to the bottom thereof, with an artificial foot. An ankle pressure cylinder forms therein an air chamber receiving therein an air chamber piston that forms therein a hydraulic fluid compartment. A hydraulic fluid supplementing cylinder and a one-way hydraulic fluid cylinder are arranged at one side of the ankle pressure cylinder and are connected via a connection piping system to the hydraulic fluid compartment. The one-way hydraulic fluid cylinder receives therein a push rod and the hydraulic fluid cylinder piston. When the structure is put into operation to allow a user to step forwards, the ankle pressure cylinder can provide both functions of hydraulic cushioning and air pressure regulation.

6 Claims, 15 Drawing Sheets

VACUUM SUCTION STRUCTURE OF ANKLE JOINT AND SUPPORT BARREL OF ARTIFICIAL LIMB

TECHNICAL FIELD OF THE INVENTION

The present invention generally relates to a vacuum suction structure of ankle joint and support barrel of artificial limb, and more particularly to a structure that uses the reaction force induced by contact of an artificial foot connect to an artificial ankle joint with the ground to drive a push rod for moving a hydraulic fluid cylinder piston to generate an effect of hydraulic cushioning and at the same time to cause a movement of an air chamber piston to make air contained in an air chamber to flow through an airflow passage to a one-way valve seat to thereby simultaneously achieve hydraulic cushioning and air pressure regulation by means of the one-way valve seat.

DESCRIPTION OF THE PRIOR ART

The development of medical science causes significant and increasing progress of medical practices and technology. With the advance of the modern era, artificial limbs are designed with inclusion of pneumatic and/or hydraulic cushioning mechanism to provide improved effects of shock absorption. Most of the users of the artificial limbs have a residuum of natural limb that is coupled to an artificial limb via a support barrel. An air conduit is connected between the support barrel and an air suction assembly. The action of stepping forward of a user causes the air suction assembly to cyclically and repeatedly draw in and release air in order to maintain the contact engagement between the limb residuum and the interior of the support barrel in a condition of complete tightness and comfortableness.

The air suction assembly is arranged independently outside the artificial limb, no matter what type of cushioning mechanism is used in the artificial limb. During forward marching, due to different habitual behaviors among different users or due to variations of road conditions, the cushioning mechanism and the air suction assembly are generally operated as two separate structures to respectively effect cushioning and air suction/air-tight engagement. This makes it hard to reduce the overall size and thus further improvement is desired.

SUMMARY OF THE INVENTION

To overcome the shortcomings of the prior art, the present invention provides a vacuum suction structure of ankle joint and support barrel of artificial limb, which comprises an ankle pressure cylinder, which forms therein an air chamber and a spring biasingly supporting an air chamber piston, and the air chamber piston forming therein a hydraulic fluid compartment and coupled to a positioning bar. A hydraulic fluid supplementing cylinder and a one-way hydraulic fluid cylinder are arranged at one side of the ankle pressure cylinder. The one-way hydraulic fluid cylinder receives therein a push rod and a hydraulic fluid cylinder piston, by which the one-way hydraulic fluid cylinder forms an upper hydraulic fluid compartment and a lower hydraulic fluid compartment. The reaction force induced by the contact between an artificial foot and the ground causes the push rod to drive the hydraulic fluid cylinder piston to move vertically, causing internal pressure to guide hydraulic fluid. A connection piping system is connected to the hydraulic fluid compartment to cause the air chamber piston to move. The one-way valve seat is set at an opposite side of the ankle pressure cylinder and is connected to an airflow passage. The one-way valve seat receives therein an air valve assembly and an U-shaped sealing member. Further, the downward movement of the air chamber piston, together with the air valve assembly, sucks in air to improve tightness of engagement of the support barrel. The upward movement of the piston then discharges air to the U-shaped sealing member to flow outside therethrough top achieve simultaneously hydraulic cushioning and air pressure regulation by means of the one-way valve seat.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
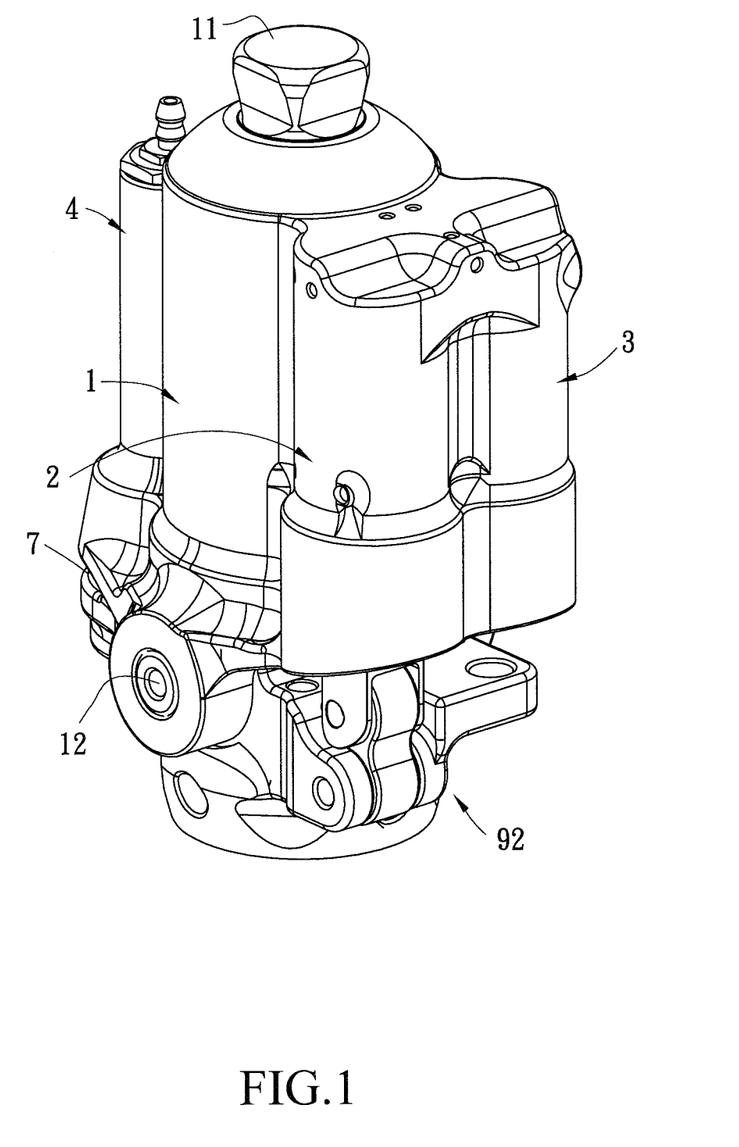
FIG. 1 is a perspective view of the present invention.
Figure 2:
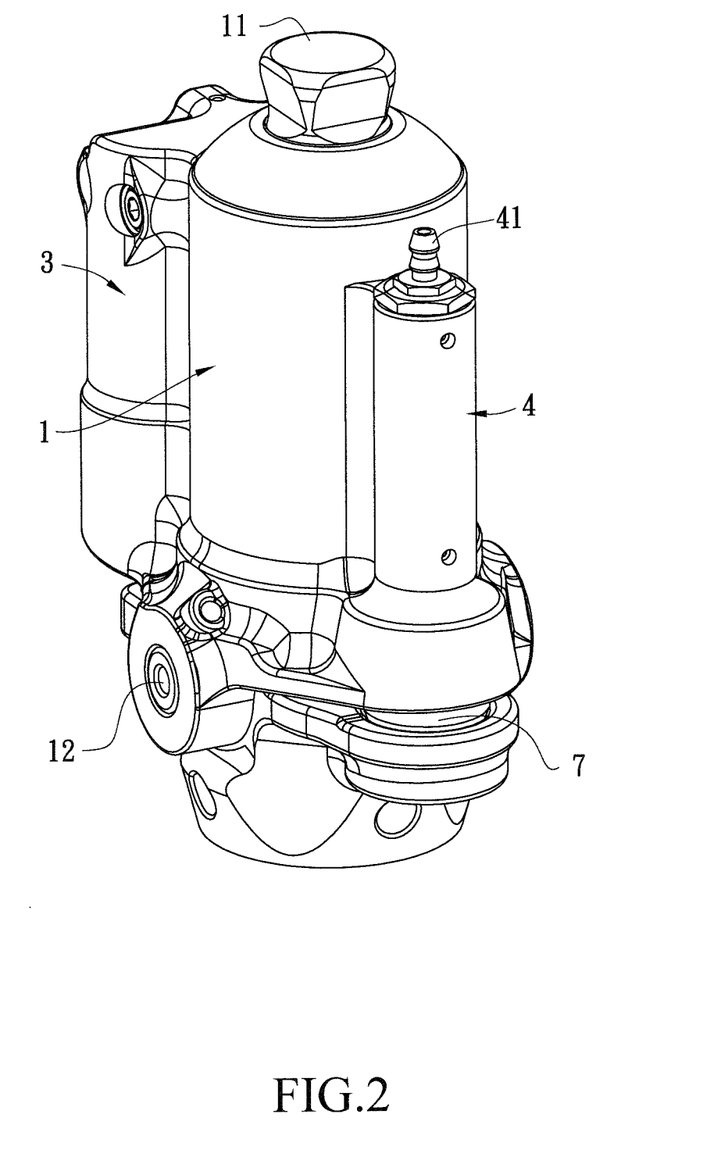
FIG. 2 is another perspective view of the present invention.
Figure 3:
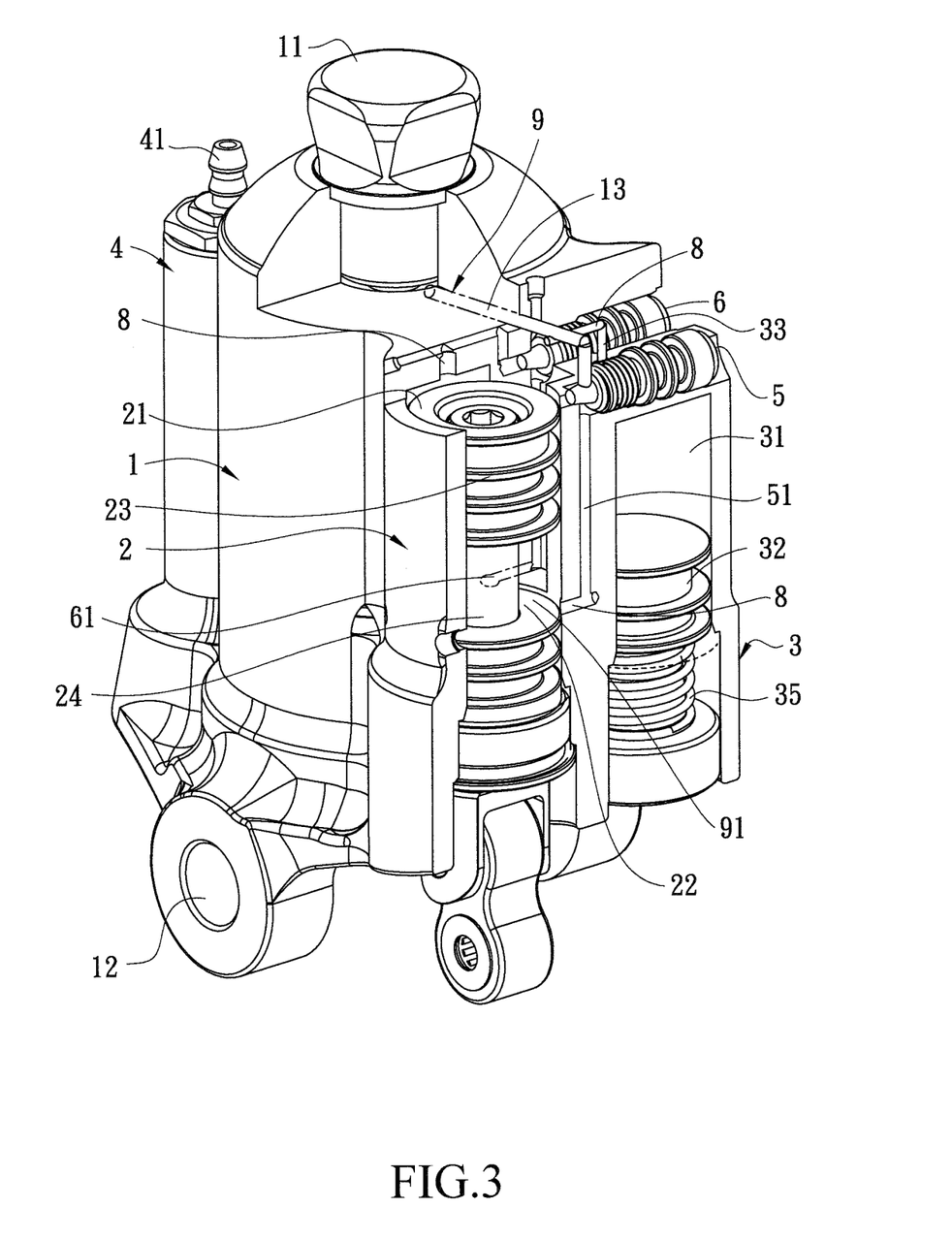
FIG. 3 is a perspective view, partially broken, showing the present invention.
Figure 4:
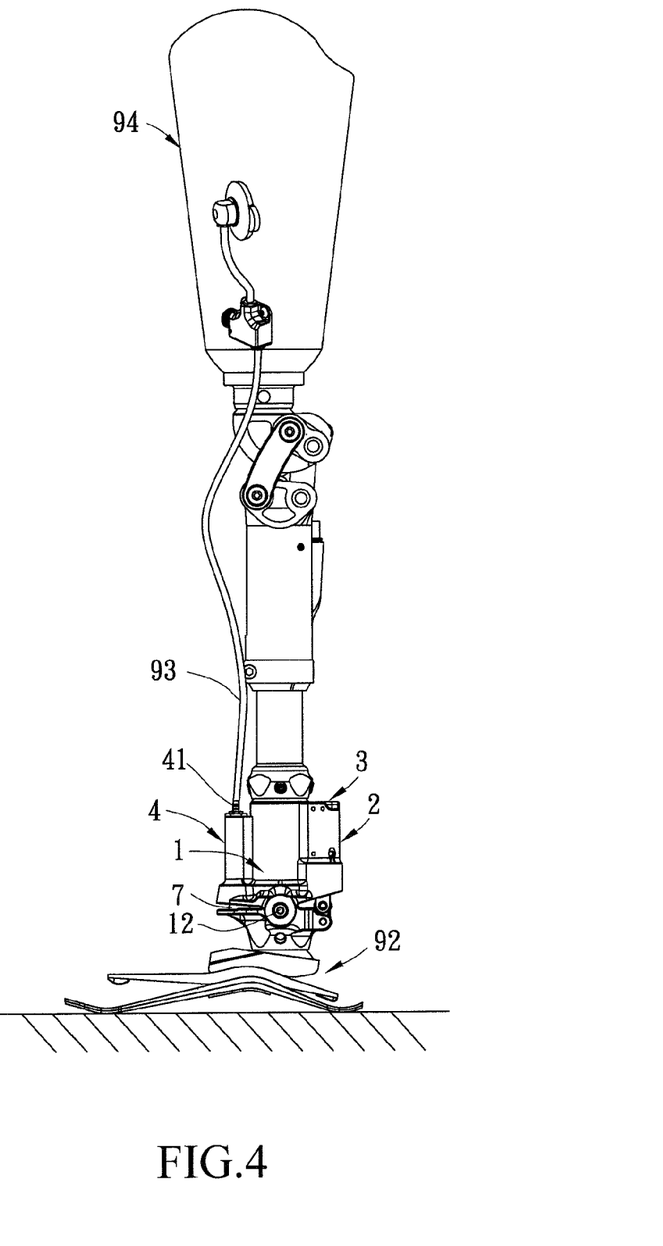
FIG. 4 is a schematic view showing an artificial limb embodying the present invention before movement.
Figure 4A:
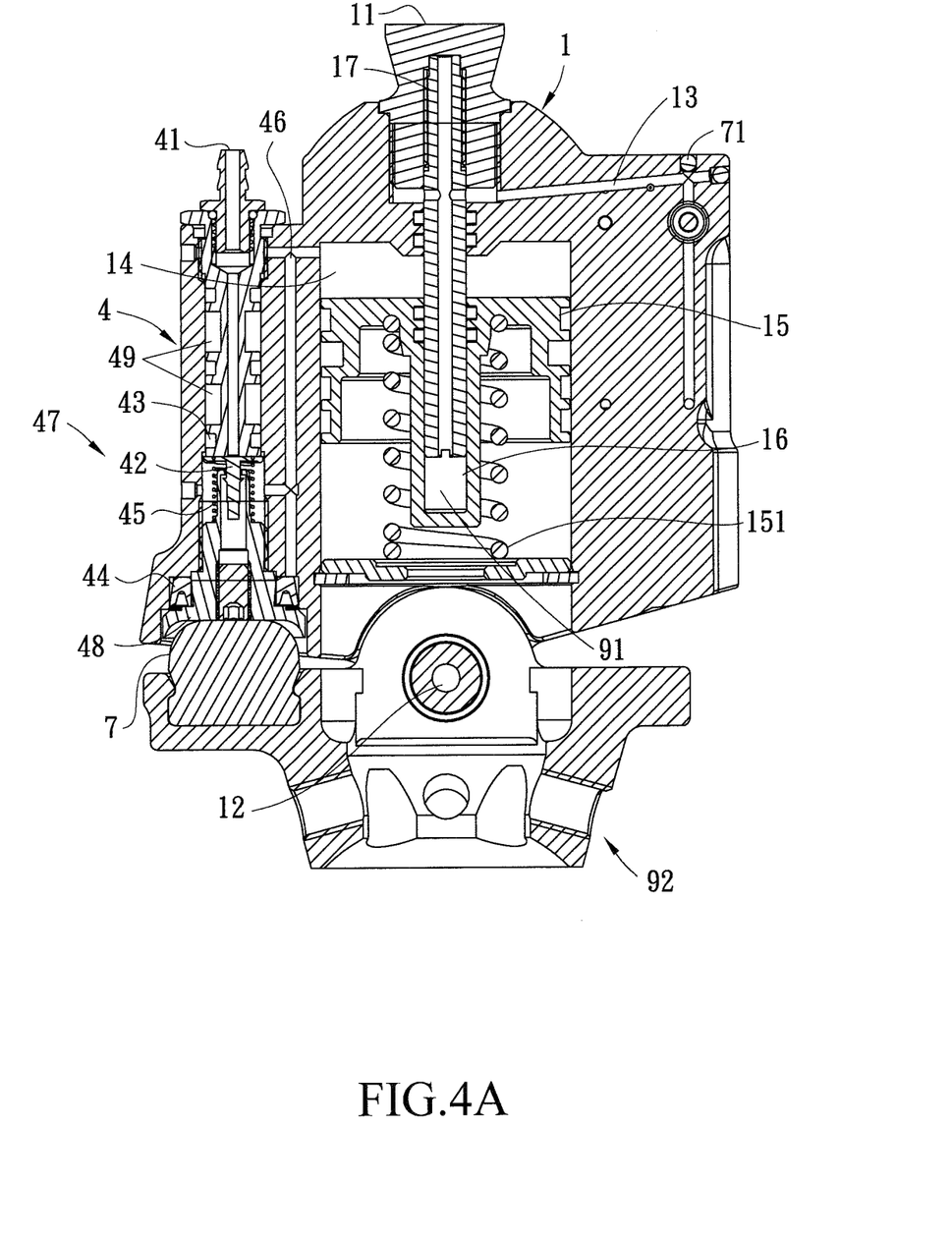
FIG. 4A is a cross-sectional view showing the present invention before movement.
Figure 4B:
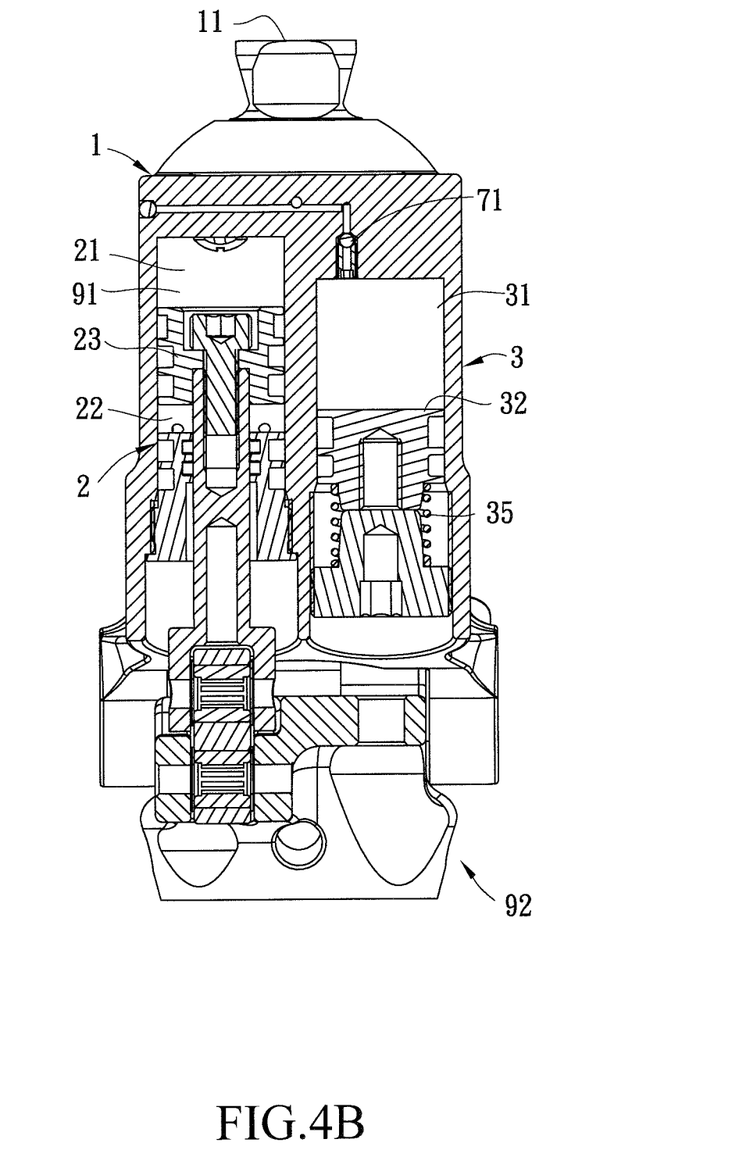
FIG. 4B is another cross-sectional view showing the present invention before movement.
Figure 5:
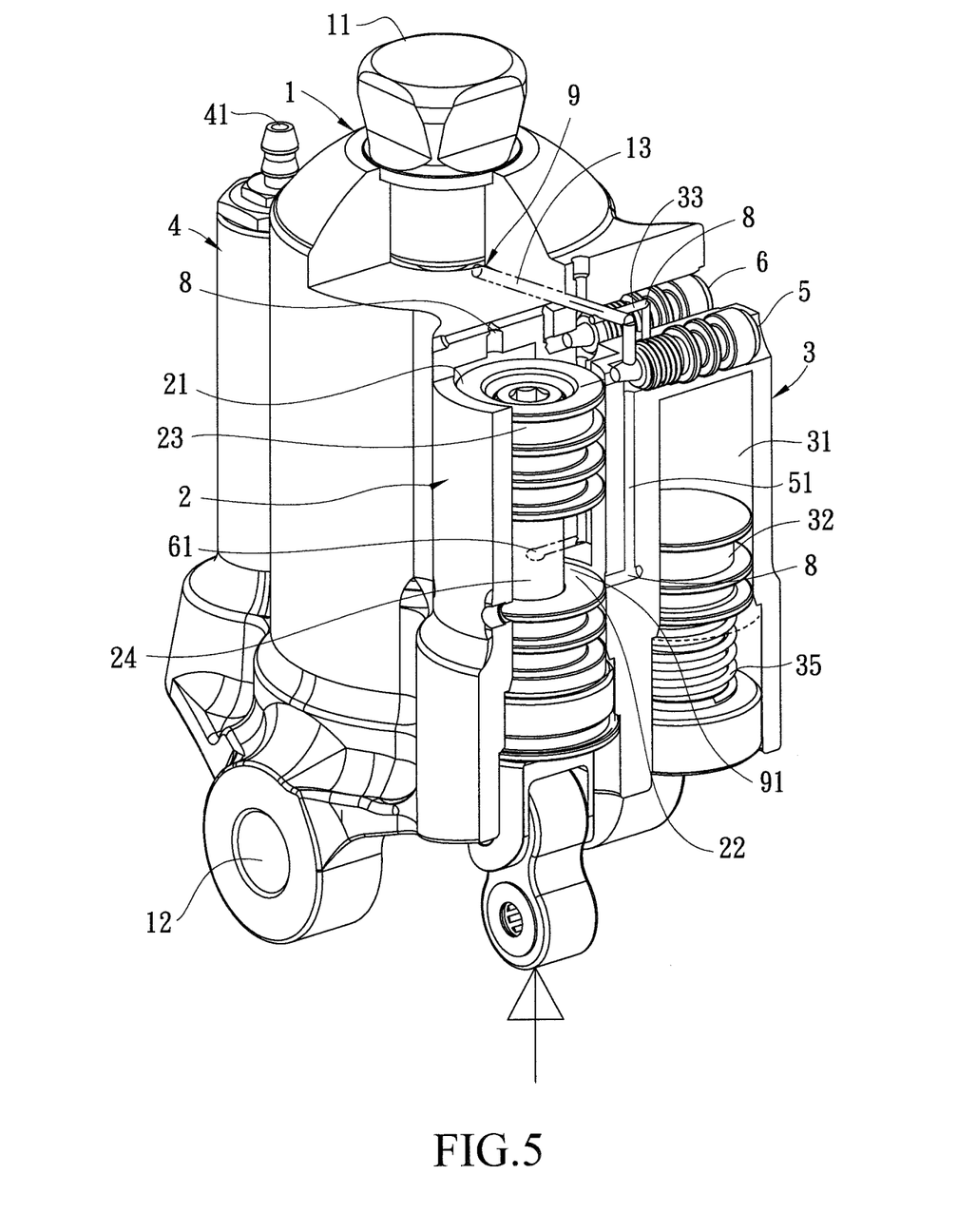
FIG. 5 is a schematic view showing the present invention moving upward.
Figure 6:
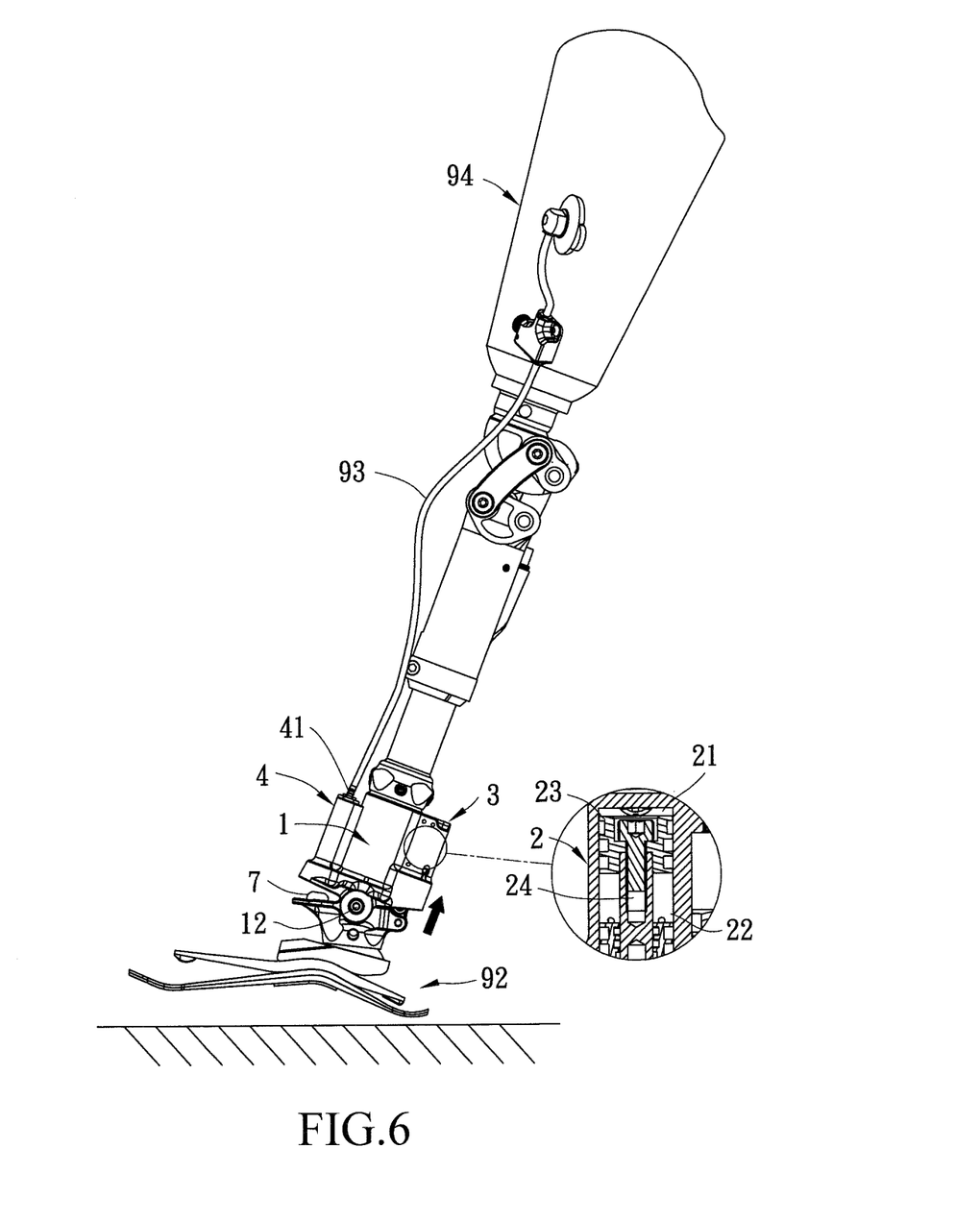
FIG. 6 is a schematic view showing an artificial limb embodying the present invention moving upward.
Figure 6A:
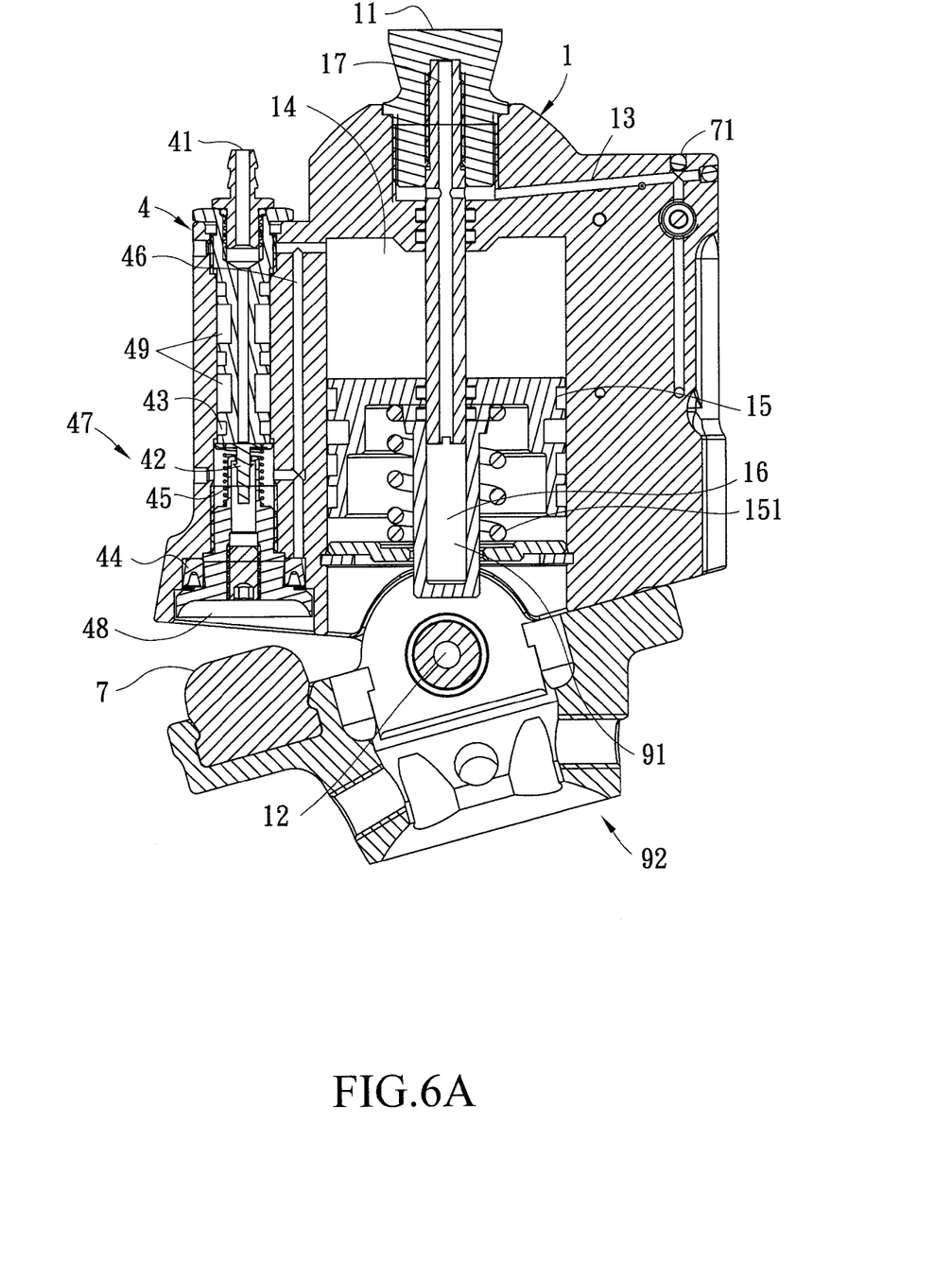
FIG. 6A is a cross-sectional view illustrating air suction and hydraulic fluid discharging from a one-way cylinder when the present invention moves upward.
Figure 6B:
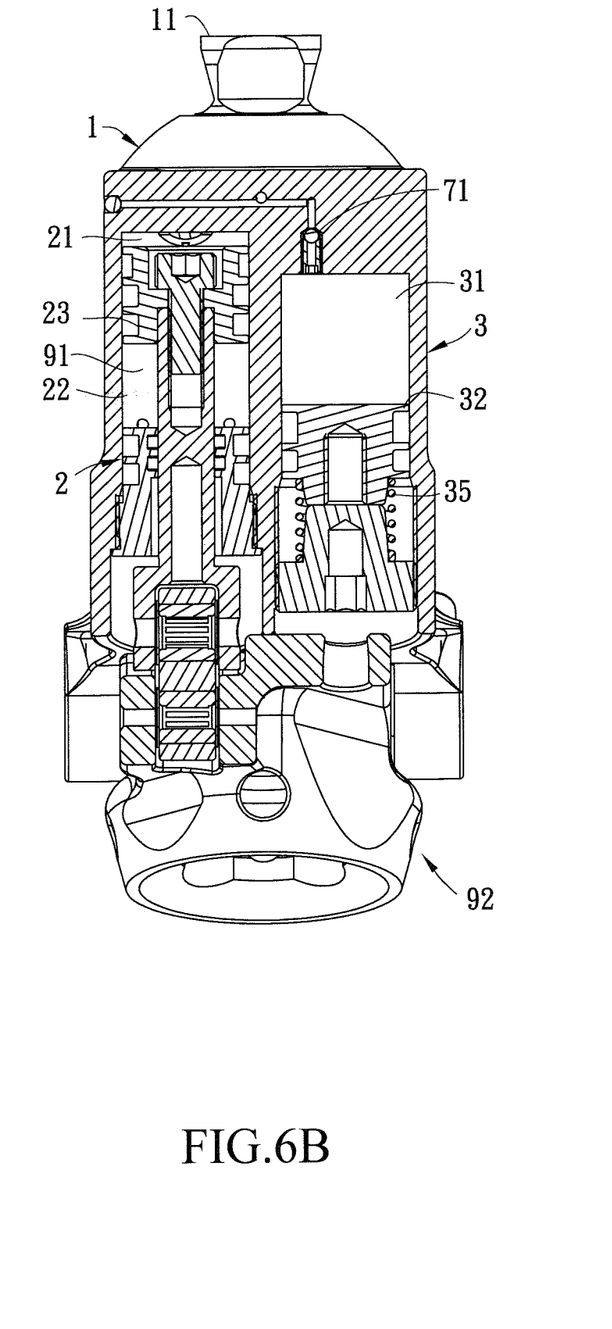
FIG. 6B is another cross-sectional view illustrating air suction and hydraulic fluid discharging from the one-way cylinder when the present invention moves upward.
Figure 7:
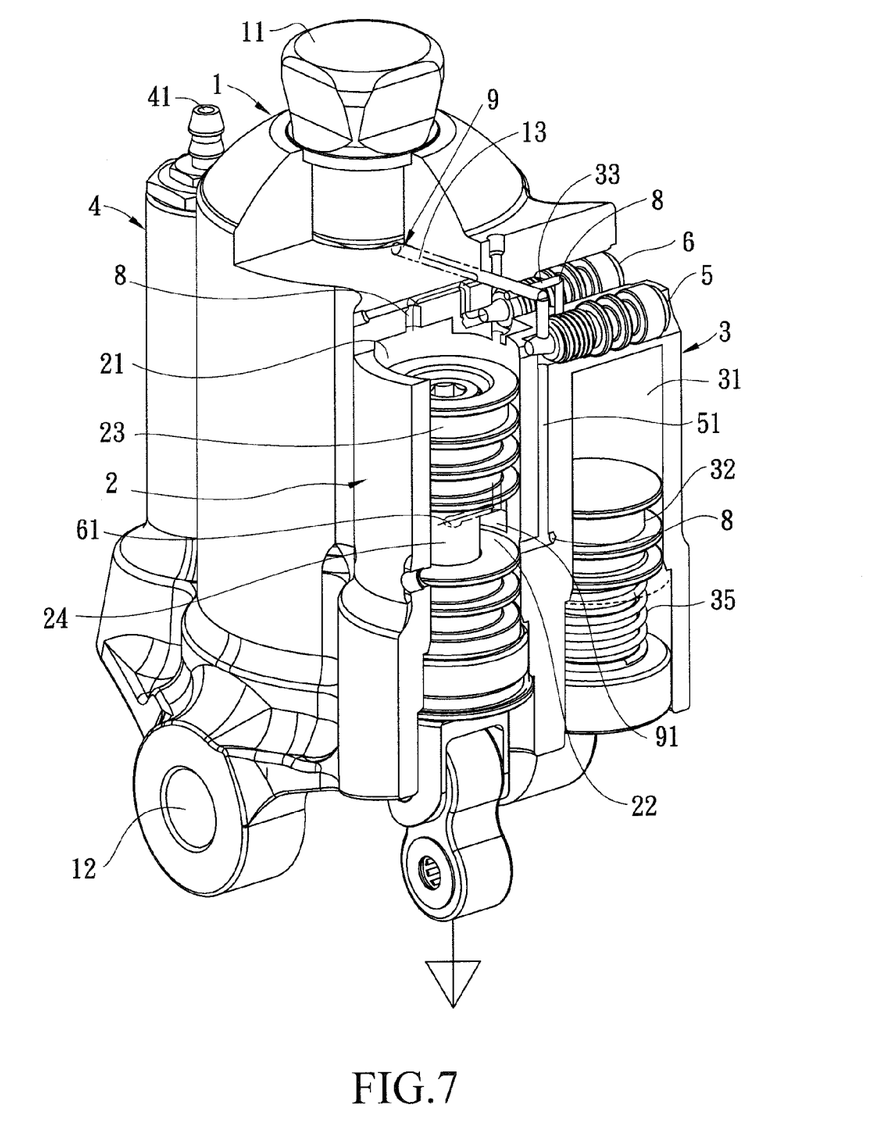
FIG. 7 is a schematic view showing the present invention moving downward.
Figure 8:
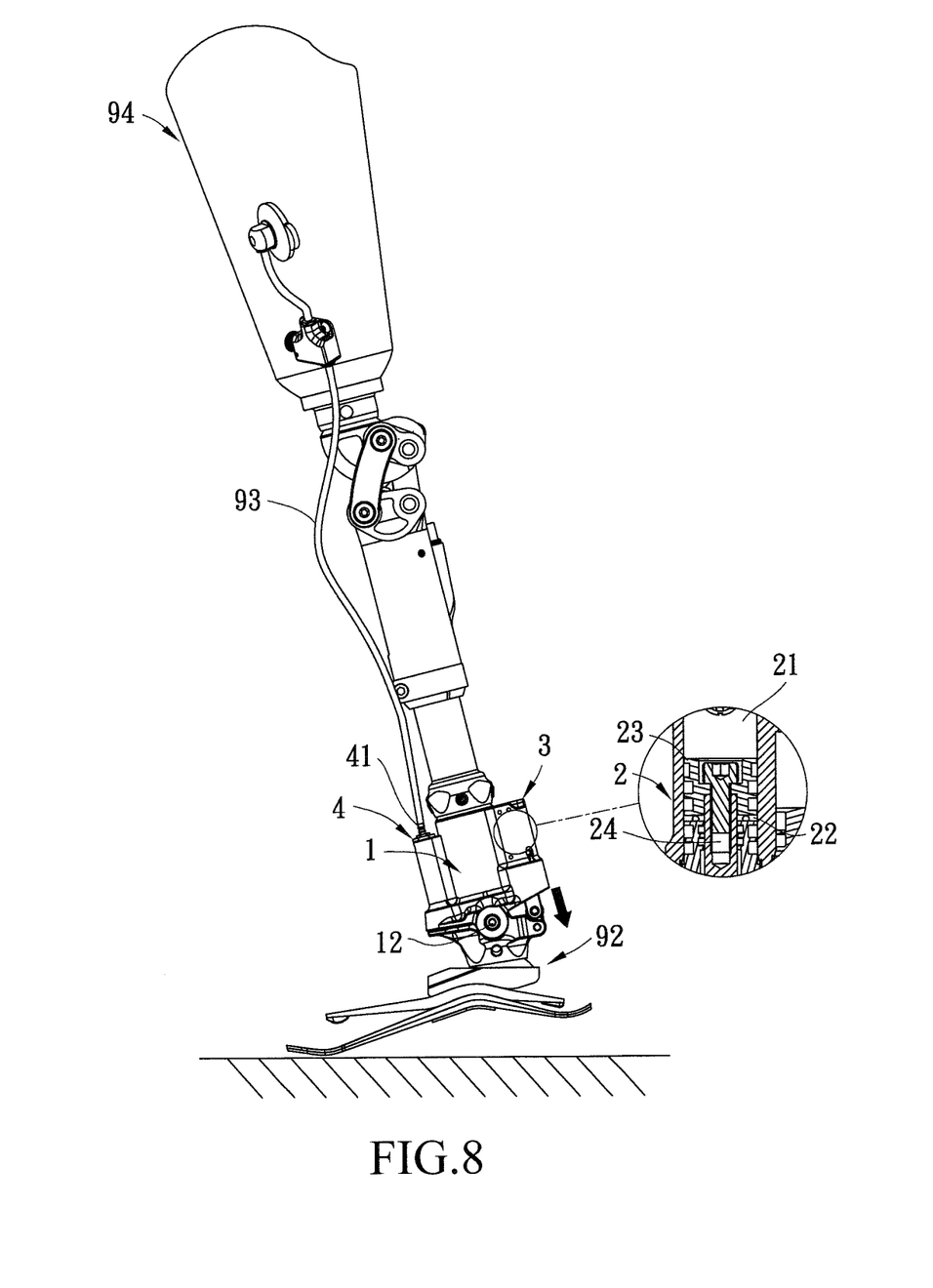
FIG. 8 is a schematic view showing an artificial limb embodying the present invention moving downward.
Figure 8A:
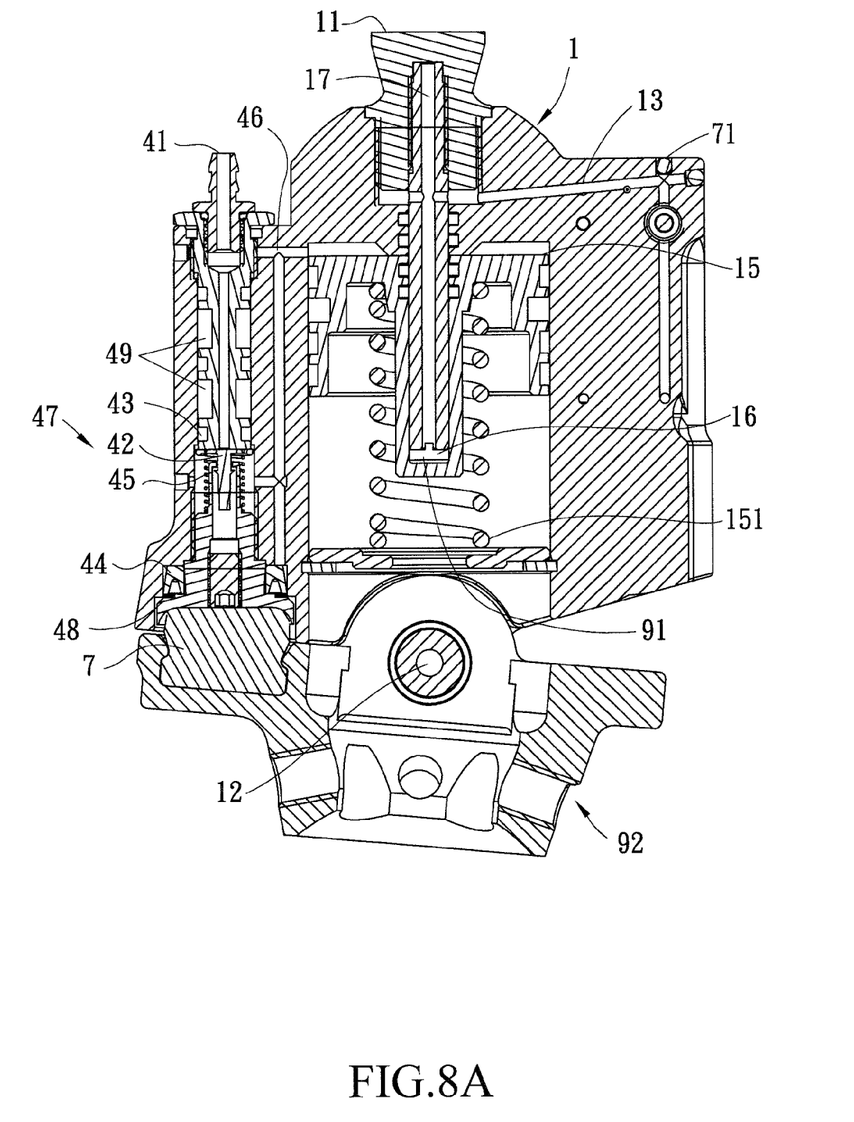
FIG. 8A is a cross-sectional view illustrating air discharge and hydraulic fluid drawn into the one-way cylinder when the present invention moves downward.
Figure 8B:
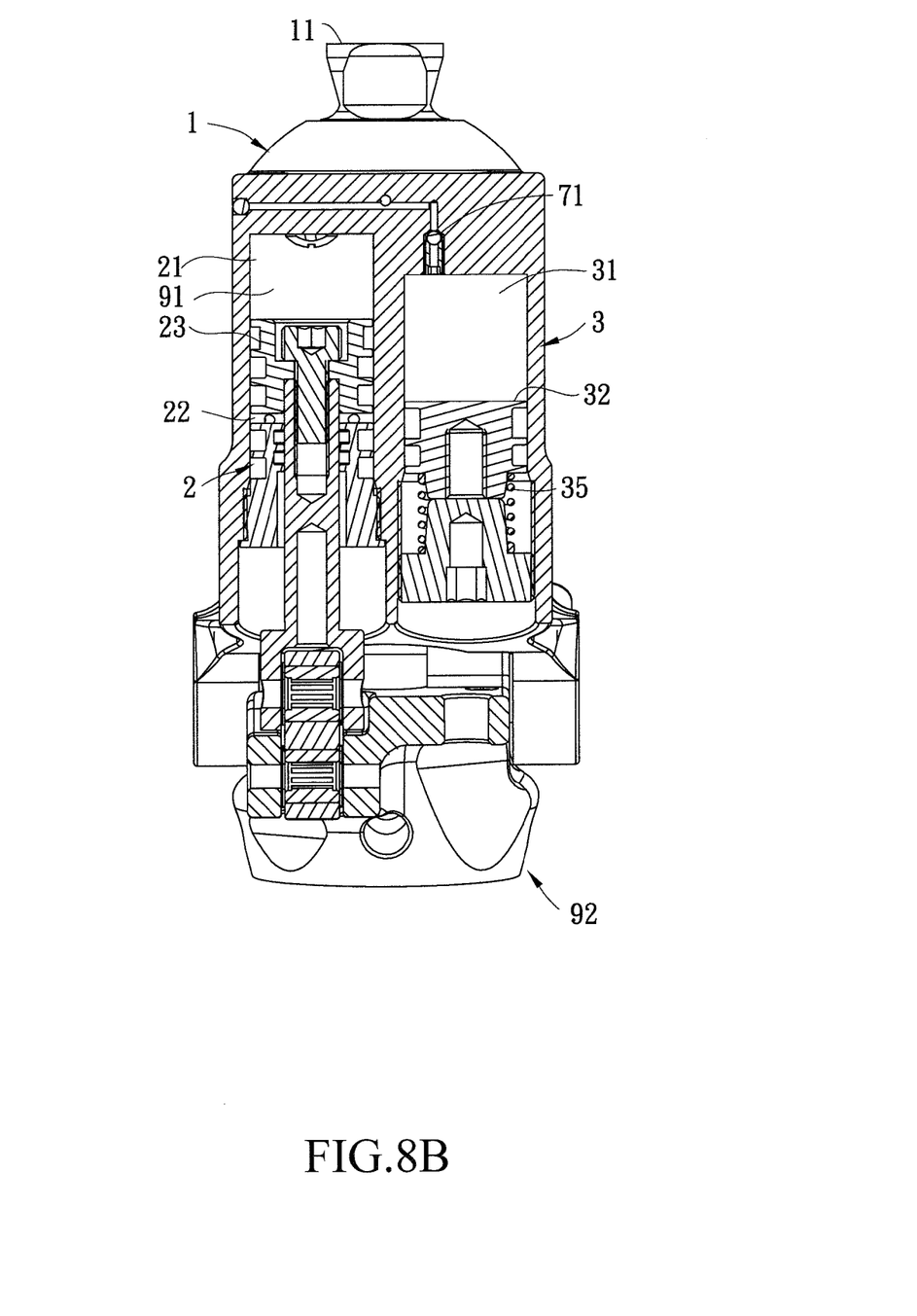
FIG. 8B is another cross-sectional view illustrating air discharge and hydraulic fluid drawn into the one-way cylinder when the present invention moves upward.
Figure 9:
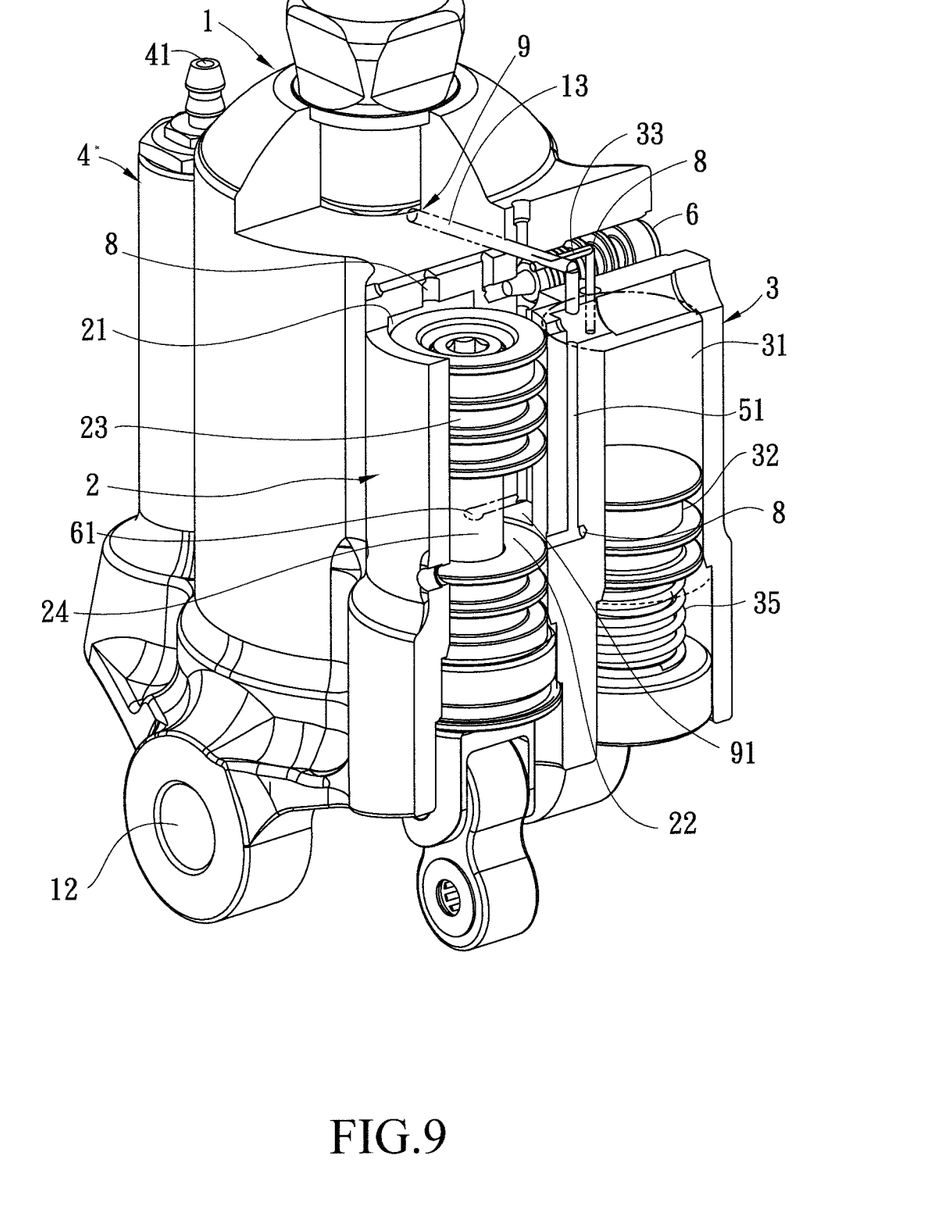
FIG. 9 is a schematic view showing the operation of a hydraulic fluid supplementing cylinder of the present invention.

The present invention will be described with reference to a preferred embodiment and the attached drawings in order to provide a full understanding of the present invention. Referring to FIGS. 1-9, the present invention provides a vacuum suction structure of ankle joint and a support barrel of an artificial limb, which comprises an ankle pressure cylinder 1 having a top to which an adjustable bolt 11 is mounted for coupling to an artificial limb and a support barrel 94 for connection with a residuum of a natural limb and a bottom that is coupled, via an ankle axle 12, to an artificial foot 92. The ankle pressure cylinder 1 comprises an air chamber 14 formed therein. The air chamber 14 receives therein a spring 151 biasingly supports an air chamber piston 15. The air chamber piston 15 comprises a hydraulic fluid compartment 16 formed therein and coupled to a positioning bar 17. A hydraulic fluid supplementing cylinder 3 and a one-way hydraulic fluid cylinder 2 are arranged at one side of the ankle pressure cylinder 1. The hydraulic fluid supplementing cylinder 3 receives therein a spring 35 biasingly supports a hydraulic fluid supplementing piston 32 to form a hydraulic fluid supplementing compartment 31. Arranged atop the hydraulic fluid supplementing cylinder 3 are a hydraulic fluid inlet valve 5 and a hydraulic fluid outlet valve 6. The one-way hydraulic fluid cylinder 2 receives therein a push rod 24 to which a hydraulic fluid cylinder piston 23 is fit in such a way that the hydraulic fluid cylinder piston 23 defines at upper and lower sides thereof an upper hydraulic fluid compartment 21 and a lower hydraulic fluid compartment 22 within the cylinder 2. A connection piping system 9 connects among the ankle pressure cylinder 1, the hydraulic fluid supplementing cylinder 3, and the one-way hydraulic fluid cylinder 2. The connection piping system 9 is filled therein with a hydraulic fluid 91 and comprises one or more one-way valves 8 to constrain flowing directions of the hydraulic fluid 91. A one-way valve seat 4 is arranged at an opposite side of the ankle pressure cylinder 1. The one-way valve seat 4 has a top to which an air-drawing joint 41 is mounted and a bottom to which a bolt 48 is mounted. The one-way valve seat 4 receives an air valve assembly 47, a second air chamber 49, and an airflow passage 46 formed therein. The airflow passage 46 is connected to the air chamber 14 to allow air to flow to the air valve assembly 47. The bolt 48 has a circumference around which a U-shaped sealing member 44 is fit.

Referring to FIGS. 1-4B, the air valve assembly 47 comprises a valve plate 42 that is arranged in combination with an O-ring 43 and is biasingly supported by a spring 45. The O-ring 43 can be adjusted by a professional technician for fluid communication between the secondary air chamber 49 and the air chamber 14 in order to control internal pressure level of the one-way valve seat 4 to suit different users for comfortableness. The connection piping system 9 comprises a hydraulic fluid supplementing passage 33, a hydraulic fluid inlet passage 51, a hydraulic fluid outlet passage 61, and a hydraulic fluid channel 13. The hydraulic fluid supplementing passage 33 connects to the hydraulic fluid channel 13 and the hydraulic fluid supplementing cylinder 3. The hydraulic fluid inlet passage 51 connects to the hydraulic fluid inlet valve 5 and the hydraulic fluid channel 13. The hydraulic fluid outlet passage 61 connects to the hydraulic fluid outlet valve 6, the hydraulic fluid outlet passage 61, the hydraulic fluid channel 13, and the one-way hydraulic fluid cylinder 2. The hydraulic fluid channel 13 connects to the above-discussed passages and also connects to the hydraulic fluid compartment 16. The hydraulic fluid supplementing passage 33 that connects to the hydraulic fluid supplementing cylinder 3 receives therein a sphere 71, and the sphere 71 is set in communication, via the connection piping system 9, with the internal pressures of the ankle pressure cylinder 1 and the one-way hydraulic fluid cylinder 2, whereby when the present invention is put into operation, the sphere 71 helps keep the hydraulic fluid supplementing passage 33 open and the hydraulic pressure steady. Thus, in case of loss of the internal hydraulic fluid of the ankle pressure cylinder 1, supplement of the hydraulic fluid can be automatically made from the hydraulic fluid supplementing cylinder 3.

Referring to FIGS. 5-9, when a user of the present invention steps forward, the artificial foot 92 connected under the ankle pressure cylinder 1 is caused to rotate about the ankle axle 12, causing the push rod 24 to push the hydraulic fluid cylinder piston 23 upwards, whereby the hydraulic fluid 91 contained in the upper hydraulic fluid compartment 21 is driven out to flow to the hydraulic fluid inlet passage 33 and the hydraulic fluid channel 13, so that the hydraulic fluid 91 is guided to the lower hydraulic fluid compartment 22 and the hydraulic fluid compartment 16, causing the air chamber piston 15 to move downward within the ankle pressure cylinder 1. Under such a condition, the U-shaped sealing member 44 is acted upon by the variation of pressure to effect air tightness, whereby the air chamber 14, operating in combination with the airflow passage 46 and the air valve assembly 47, draws in air from the support barrel 94 via the air conduit 93 and the air-drawing joint 41. Under such a condition, the valve plate 42 of the air valve assembly 47 is acted upon by the air pressure and deflects to allow the air to be drawn into the air chamber 14 of the ankle pressure cylinder 1, thereby providing a suction force that effects air tightness of engagement between the limb residue and the support barrel 94 to prevent undesired separation and ensure excellent engagement of contact. When the artificial foot 92 subsequently rotates downward, the push rod 24 drives the hydraulic fluid cylinder piston 23 to move downwards, compressing the hydraulic fluid 91 contained in the lower hydraulic fluid compartment 22 to flow through the hydraulic fluid outlet passage 61 and the hydraulic fluid channel 13, whereby the hydraulic fluid 91 in the hydraulic fluid compartment 16 and the lower hydraulic fluid compartment 22 is guided into the upper hydraulic fluid compartment 21 and the air chamber piston 15 moves upward to allow air to discharge from the air chamber 14 through the airflow passage 46. Due to the restraint imposed by the air valve assembly 47 and the rotation of the U-shaped sealing member 44, air is discharged smoothly via the one-way valve seat 4 to the outside. The U-shaped sealing member 44 is acted upon by the pressure of air to inwardly collapse, forming a gap between the U-shaped sealing member 44 and the bolt 48 through which the internal air is smoothly discharged to the outside of the one-way valve seat. The artificial foot 92, which can be brought by rotation thereof to engage the bolt 48, is provided with an elastic rubber block 7. The elastic rubber block 7 is engageable with the bolt 48, by which the contact impact can be alleviated. According to the above description, it can be seen that in marching forward, a reaction force induced by the contact between the artificial foot and the ground can drive the push rod to perform a series of actions by which the entire structure can simultaneously perform hydraulic cushioning and air pressure regulation by means of the one-way valve seat.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. A prosthetic attachment system including a vacuum suction structure, an ankle joint, a support barrel and an artificial limb, the vacuum suction structure comprising: an ankle pressure cylinder that forms therein an air chamber, the air chamber receiving therein a spring biasingly supporting an air chamber piston, the air chamber piston comprising a hydraulic fluid compartment formed therein and coupled to a positioning bar; a hydraulic fluid supplementing cylinder and a one-way hydraulic fluid cylinder arranged at one side of the ankle pressure cylinder, the hydraulic fluid supplementing cylinder receiving therein a spring biasingly supporting a hydraulic fluid supplementing piston that defines a hydraulic fluid supplementing compartment, the hydraulic fluid supplementing cylinder being provided atop with a hydraulic fluid inlet valve and a hydraulic fluid outlet valve; the one-way hydraulic fluid cylinder receiving therein a push rod to which a hydraulic fluid cylinder piston is fit to define, in upper and lower sides thereof, an upper hydraulic fluid compartment and a lower hydraulic fluid compartment; a connection piping system connecting to the ankle pressure cylinder, the hydraulic fluid supplementing cylinder, and the one-way hydraulic fluid cylinder, the connection piping system being filled with a hydraulic fluid and being provided with at least one one-way valve to constrain flowing direction of the hydraulic fluid; a one-way valve seat arranged at an opposite side of the ankle pressure cylinder, the one-way valve seat being provided, at a top thereof, with an air-drawing joint and being also provided, at a bottom thereof, with a bolt and receiving therein an air valve assembly, a second air chamber, and an airflow passage, the airflow passage connecting to the air chamber to allow air to flow to the air valve assembly, the bolt having a circumference around which a U-shaped sealing member is fit;

characterized in that through stepping forward, the push rod drives the hydraulic fluid cylinder piston to move vertically, compressing the hydraulic fluid to flow through the connection piping system into the hydraulic fluid compartment formed in the air chamber piston so as to drive the air chamber piston to move, whereby the air chamber piston causes, via the airflow passage, variation of density of air contained in the support barrel so that the ankle pressure cylinder achieves both hydraulic cushioning and air pressure regulation.

2. The structure according to claim 1, wherein the air valve assembly comprises a valve plate, an O-ring, and a spring, the spring biasingly supporting the O-ring and the valve plate, the O-ring regulating communication between the secondary air chamber and the air chamber formed in the ankle pressure cylinder so as to regulate intensity of suction force induced by the air valve assembly.

3. The structure according to claim 1, wherein the connection piping system comprises a hydraulic fluid supplementing passage, a hydraulic fluid inlet passage, a hydraulic fluid outlet passage, and a hydraulic fluid channel, the hydraulic fluid supplementing passage connecting to the hydraulic fluid channel and the hydraulic fluid supplementing cylinder, the hydraulic fluid inlet passage connecting to the hydraulic fluid inlet valve and the hydraulic fluid channel, the hydraulic fluid outlet passage connecting to the hydraulic fluid outlet valve, the hydraulic fluid outlet passage, the hydraulic fluid channel, and the one-way hydraulic fluid cylinder, the hydraulic fluid channel connecting to the hydraulic fluid compartment.

4. The structure according to claim 3, wherein the hydraulic fluid inlet passage is constructed such that an upward movement of the hydraulic fluid cylinder piston reduces internal volume of the upper hydraulic fluid compartment so that the hydraulic fluid is caused to flow through the hydraulic fluid inlet passage and the hydraulic fluid channel to the lower hydraulic fluid compartment and the hydraulic fluid compartment to make downward movement of the air chamber piston, whereby the air chamber operates, in combination with the airflow passage, the air valve assembly, and the air-drawing joint, to generate suction that draws in air.

5. The structure according to claim 3, wherein the hydraulic fluid outlet passage is constructed so that a downward movement of the hydraulic fluid cylinder piston reduces internal volume of the lower hydraulic fluid compartment, causing the hydraulic fluid to flow through the hydraulic fluid outlet passage and the hydraulic fluid channel, so that the hydraulic fluid contained in the hydraulic fluid compartment and the lower hydraulic fluid compartment is conducted to the upper hydraulic fluid compartment to make upward movement of the air chamber piston, whereby the air chamber operates, in combination with the airflow passage, the air valve assembly, and the U-shaped sealing member, to generate an effect of discharging air.

6. The structure according to claim 3, wherein the hydraulic fluid supplementing passage is constructed so as to supply the hydraulic fluid through the hydraulic fluid channel to the hydraulic fluid compartment to effect automatic supplementing in case of shortage of hydraulic fluid.

* * * * *